United States Patent [19]

Sih et al.

[11] E Re. 29,990

[45] Reissued May 8, 1979

[54] PROCESSES FOR STEREOSPECIFICALLY PREPARING CHIRAL 2-SUBSTITUTED-4-HYDROXY-2-CYCLOPENTEN-1-ONE

[75] Inventors: Charles J. Sih, Madison; James B. Heather, Middleton, both of Wis.

[73] Assignee: Wisconsin Alumni Research Foundation, Madison, Wis.

[21] Appl. No.: 848,618

[22] Filed: Nov. 4, 1977

Related U.S. Patent Documents

Reissue of:

[64] Patent No.: 3,968,141
Issued: Jul. 6, 1976
Appl. No.: 478,713
Filed: Jun. 12, 1974

U.S. Applications:

[63] Continuation of Ser. No. 309,766, Nov. 27, 1972, abandoned.

[51] Int. Cl.[2] ..... C07C 51/00; C07C 61/38

[52] U.S. Cl. ..... 560/121; 546/35; 195/30; 260/410.5; 260/410.9 R; 260/413; 260/456 R; 260/456 P; 560/106

[58] Field of Search ..... 562/503; 560/121; 562/503; 260/456 R, 456 P

[56] References Cited

U.S. PATENT DOCUMENTS 3,773,622 11/1973 Sih ..... 195/51

OTHER PUBLICATIONS

Pappo et al., Tet. Letters, 2627, (1972).

*Primary Examiner*—Robert Gerstl
*Attorney, Agent, or Firm*—Howard W. Bremer

[57] ABSTRACT

A method for stereospecifically preparing chiral 2-substituted-4-hydroxy-2-cyclopenten-1-one which comprises asymmetrically reducing 2-substituted cyclopentane-1,3,4-trione to the corresponding 2-substituted-4(R)-hydroxy-cyclopentane-1,3-dione, enolizing the said dione to obtain the enol ester or enol ether configuration, reducing the enol ester or ether and recovering the desired compound. The chiral 2-substituted-4-hydroxy-2-cyclopenten-1-one are key intermediates in the preparation of prostaglandins.

9 Claims, No Drawings

PROCESSES FOR STEREOSPECIFICALLY PREPARING CHIRAL 2-SUBSTITUTED-4-HYDROXY-2-CYCLOPENTEN-1-ONE

Matter enclosed in heavy brackets [ ] appears in the original patent but forms no part of this reissue specification; matter printed in italics indicates the additions made by reissue.

This application is a continuation of application Ser. No. 309,766, filed Nov. 27, 1972 now abandoned.

The invention described herein was made in the course of work under a grant or award from the Department of Health, Education, and Welfare.

This invention relates to methods for preparing certain stereospecific compounds which are key intermediates in the preparation of prostaglandins or prostaglandin-like compounds.

More specifically this invention relates to processes for preparing chiral 2-substituted-4-hydroxy-2-cyclopenten-1-one.

Still more specifically this invention relates to processes for preparing 2-(6'-carbomethoxyhexyl)-4(R)-hydroxy-2-cyclopenten-1-one, a compound which is a key intermediate in the preparation of prostaglandins.

The prostaglandins, which are cyclic, oxygenated, $C_{20}$ fatty acids based upon the prostanoic acid skeleton, are believed to have great potential as therapeutic agents because of the widespread physiologic responses which they elicit in the cardiovascular, nervous, reproductive, renal and gastric systems upon administration to animals including man. The supply of these materials is currently very limited and, in general, methods which have been disclosed for making them entail the use of tedious resolution procedures to obtain the desired optically active compounds.

It is a principal purpose of this invention to provide processes for preparing chiral compounds which are key intermediates in the preparation of prostaglandins or prostaglandin-like compounds.

Broadly, this invention relates to processes for preparing 2-substituted-4(R)-hydroxy-2-cyclopenten-1-one by asymmetrically reducing a 2-substituted-cyclopentane-1,3,4-trione to the corresponding 2-substituted-4(R)-hydroxy-cyclopentane-1,3-dione, subjecting the dione to enolization for the formation of the enol ester or enol ether configuration through selective O-acylation or O-alkylation under conditions which preferentially promote acylation or alkylation of the oxygen at the C-1 position separating the substituted C-1 ester or enol ether from any substituted C-3 enol ester or enol ether formed, and reducing the substituted C-1 enol ester or enol ether to obtain 2-substituted-4-(R)-hydroxy-2-cyclopenten-1-one which is recovered from the reduction reaction mixture.

This process is readily depicted in the following reaction sequence:

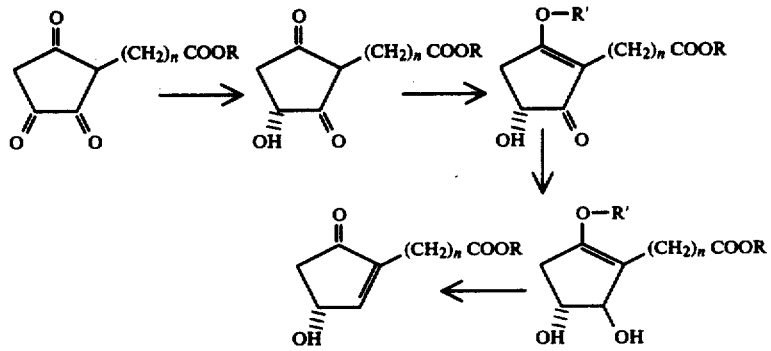

where R is a hydrocarbon radial containing from about 1 to 4 carbon atoms or benzyl n is an integer from about 1 to 12, the hydrocarbon chain represented by $(CH_3)_n$ being saturated or containing unsaturation at the 5-6 position in the equivalent acid side chain represented by $(CH_2)_nCOOH$ and where the unsaturation comprises a cis double bond or a triple bond and R' has the respective identities set forth hereinafter.

Previously, R. Pappo et al. in Annals of the New York Academy of Sciences, Vol. 180, p. 64 (1971), showed the following method for preparing the methyl enol ether from 2-(6'-carbomethoxyhexyl)-4-hydroxycyclopenten-1,3-dione:

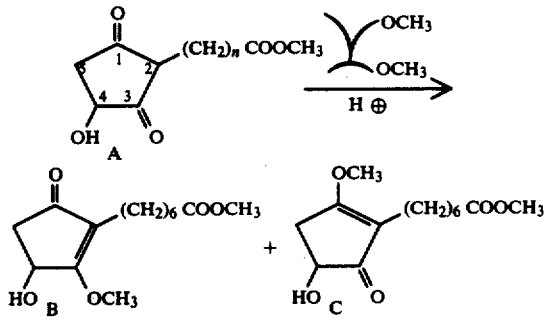

The procedure was carried out by refluxing the hydroxy dione ester (A) with the dimethoxypropane under acidic conditions to yield the two indicated isomeric enol esters (B and C).

The disadvantages with the Pappo et al. procedure are (1) that it gives only about 40% of the desired C-1 enol ether (C) and (2) that the asymmetric center at C-4 is destroyed.

The latter disadvantage is extremely serious in prostaglandin preparation utilizing 1,4-addition reactions, since the stereochemistry of the prostanoic acid skeleton (the C-8 and C-12 positions in prostaglandins) is dictated by the stereochemmistry at C-4.

The processes of the present invention overcome the disadvantages exhibited by the Pappo et al. process. Most importantly, the processes of this invention permit the asymmetric center at C-4 to be retained so that the 2-substituted-4-hydroxy-2-cyclopenten-1-one product is chiral, an essential characteristic where the prostaglandins are to be prepared. In addition, the processes of this invention preferentially promote acylation or alkylation of the oxygen atom at the C-1 position in the molecule, the molecular configuration which is the desired one for subsequent reduction to the desired compound, namely, 2-substituted-4(R)-hydroxy-2-cyclopenten-1-one.

Although there is no intention to be bound by theoretical consideration, it is believed that a moderately bulky group must be used for acylation so that through steric hindrance acylation preferentially occurs at the oxygenation of the C-1 position. Also, it is believed that the O-alkylation at C-1 is favored under basic conditions and that the size of the alkylating group is of less importance than in the acylation. In any event, it was found that observance of the above conditions permit the retention of the asymmetric center at C-4 and that no racemization occurs.

In the process of this invention the asymmetric reduction of the 2-substituted cyclopentane-1,3,4-trione to the corresponding 2-substituted-4(R)-hydroxy-cyclopentane-1,3-dione can be accomplished by catalytic hydrogenation in the presence of a rhodium complex with a chiral phosphine ligand as the catalyst. (Catalysts of this type are disclosed in Journ. Chem. Soc., Chem. Comm., 10, (1972) by W. S. Knowles et al.) The preferred catalyst in the present process can be designated as $L_2Rh^+CODBF_4^-$ (available from Monsanto Co., St. Louis, Mo., under the identification CP71327) where L indicates o-anisylcyclohexylmethylphosphine and COD indicates 1,5-cycloacetadiene.

A method for hydrogenating 2(6'-carbomethoxyhexyl)cyclopentane-1,3,4-trione utilizing the said preferred catalyst is set forth below.

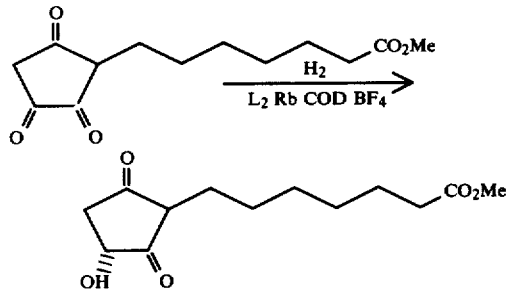

5.0 g of the 2(6'-carbomethoxyhexyl)cyclopentane-1,3,4-trione, 95.8 mg of the indicated catalyst and 2.78 ml of triethylamine were dissolved in 35 ml of methanol and subjected to hydrogenation at one atmosphere. After 92.6% of the theoretical quantity of hydrogen had been consumed the reaction was terminated by pouring the hydrogenation reaction mixture into $HCl\text{-}H_2O$ (about pH2). The resulting mixture was extracted three times with ethyl acetate the organic layers were separated and washed with sodium bicarbonate solution (5% solution) until no color appeared in the aqueous phase. The combined bicarbonate extracts were extracted with ethyl acetate, the resulting yellow aqueous layer was carefully acidified to pH 2.0 with hydrochloric acid and extracted with ethyl acetate. The organic layer was separated, dried over $Na_2SO_4$ and evaporated to dryness. The dried material was dissolved in and then crystallized from ethyl acetate giving 1.7 g of product (34% yield) having the following characteristics: u.v.$\gamma_{max}^{MeOH}$ 272 nm ($\epsilon$24,000) CD$\gamma$281 nm ($\theta = -58.3\times10^3$); $\theta = +60\times10^3$ at $\gamma$262 nm (68% optical purity). A second crop (1.6%) showed no optical activity; filtrate almost no optical activity.

The trione methyl ester, used as the starting material in the foregoing hydrogenation reaction can be readily obtained from the corresponding trione acid in accordance with the following procedure, the trione acid being readily obtainable by the method shown in Pappo et al. (supra).

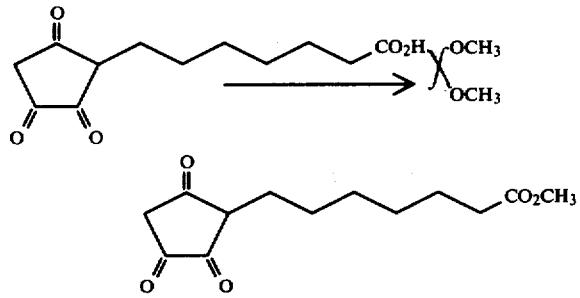

A mixture of 1 g of trione acid, 2 ml of methanol, 0.2 ml of conc HCl and 2.5 ml of dimethoxypropane was allowed to stand at room temperature overnight. The solution was then evaporated to dryness (rotary evaporator) and the residue was dissolved in 10 ml of ethyl acetate. The ethyl acetate layer was extracted with a saturated $NaHCO_3$ solution ($2\times15$ ml). The bicarbonate solution was acidified and extracted with ethyl acetate ($4\times25$ ml). This extract was washed with a saturated NaCl solution and dried over $MgSO_4$. Evaporation of solvent offered a reddish oil, which solidifed upon standing to give a yellow solid (seeding with a crystal of the trione methyl ester aids the solidifcation process).

Alternatively, the dione can be prepared microbiologically, as shown in application for U.S. patent application Ser. No. 293,457, filed Sept. 29, 1972 now U.S. Pat. No. 3,773,622, by subjecting 2-substituted-cyclopentane-1,3,4-trione or 2-substituted-3-alkoxy-2-cyclopentene-1,4-dione to the fermentative enzymatic action of a microorganism of the class Ascomycetes, or via resolution with brucine as set forth hereinafter.

2-(6'-carbomethoxyhexyl)-4-hydroxy-cyclopentane-1,3-dione(6 g, 0.002 mole) was mixed with brucine

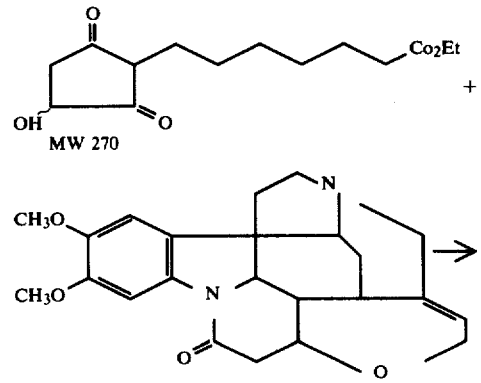

Brucine MW 395

-continued

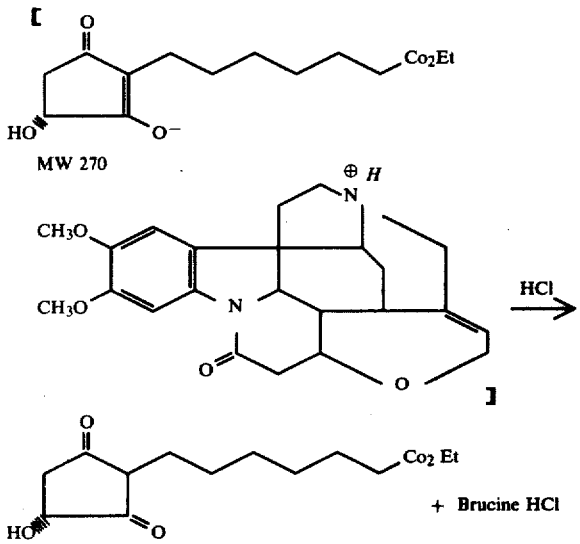

(8.7 g, 0.022 mole). To this mixture 35 ml of acetone was added and the resulting solution was refluxed under nitrogen for 15 minutes; cooled to room temperature, allowed to stand at room temperature for three hours and then at ice box temperature (40°-50° F.) overnight. The product, a brucine-hydroxydione salt, deposited as fine crystals. The crystals were filtered off on a buchner funnel, washed with cold acetone; and were recrystallized to constant rotation from ethyl acetate and Skelly B (five recrystallizations).

Rotation of the salt in $CHCl_3$

| | | |
|---|---|---|
| 2nd | recrystallization | = −28.30 |
| 3rd | " | = −31.31 |
| 4th | " | = −33.92 (C 0.56) |
| 5th | " | = −33.92 (C 0.51) |

The resolved brucine-hydroxydione salt (2.2 g) was dissolved in ethyl acetate (30 ml). To this solution 30 ml of 0.25 N HCl was added and the heterogeneous mixture was stirred very vigorously for 2 minutes. upon standing two layers formed and were separated. The aqueous layer was extracted twice with ethyl acetate. The organic layers from the two extractions were combined and were washed with water and saturated brine solution and were dried over anhydrous magnesium sulfate. Evaporation of the solvent gave 2-(6'-carbomethoxyhexyl)-4(R)-hydroxy-cyclopentane-1,3-dione as a white crystalline solid (780 mg).

As pointed out hereinbefore, the enolization of the 2-substituted dione can be accomplished for conversion to the enol ester or enol ether configuration through selective O-acylation or selective O-alkylation in accordance with the following general methods.

Enolization With Selective O-Acylation

In general, this reaction can be carried out in accordance with the following schematic procedure:

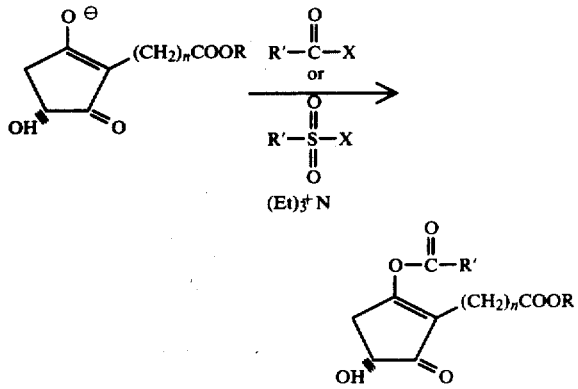

where R and n have the identities indicated above, R' is a group selected from unsubstituted or halogen-, alkyl- or alkoxy-substituted phenyl, benzyl, biphenyl or naphthyl groups, or in an alkanyl or alkenyl group having from about 1 to 6 carbon atoms, pivaloyl or isobutyl and X is iodine, chlorine, bromine, or the

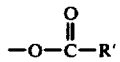

or $—OSO_2R'$ groups where R' has the above noted designation.

In the O-acylation procedure indicated it is preferable to use only one equivalent of the acylating agent since the use of excess acylating agent tends to promote acylation of the hydroxyl group as well. Also, the size of the acylating group is important to the formation of the desired enol-ester a bulkier grouping promoting the formation of more of the desired enol forms, i.e. O-acylation of the C-1 position. For example, with acetyl chloride as the acylating agent and 2(6'-carbomethoxyhexyl)-4(R)-hydroxy-2-cyclopentane-1,3-dione as the substrate the two enol acylates

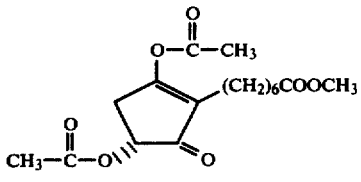

A and

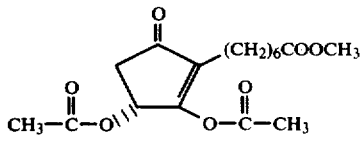

B are formed in the ratio of 70–75% of A to 30–25% of B. When, however, a more bulky acylating agent, such as pivaloyl choride is used, the ratio of the desired substituted C-1 enol pivalylate to the substituted C-3 enol pivalylate is about 90:10.

It will be readily apparent to those skilled in the art that the substituted C-1 enol sulfonates can be exchanged with alcohols to provide C-1 enol ether derivatives.

Enolization With Selective O-Alkylation

The O-alkylation reaction can be carried out in accordance with the following schematic reaction sequence:

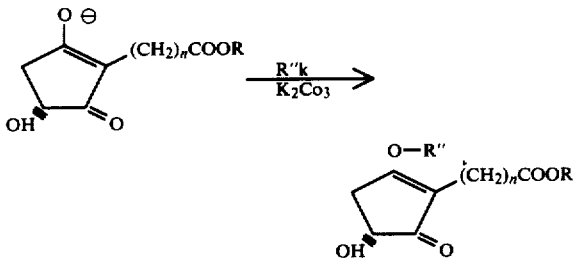

where R and n have the identities indicated above, R'' is a group selected from saturated and unsaturated alkyl having from about 1 to 6 carbon atoms, benzyl, diphenylmethyl or ester group of the formulae

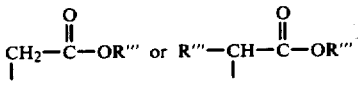

where R''' is a hydrocarbon radical containing from about 1 to 6 carbon atoms, and X is the chlorine, bromine, iodine, sulfate, isocyanate or alkyl-substituted or unsubstituted aryl sulfonate radical. When carried out under alkaline conditions no racemization was noticeable.

As noted with respect to the O-acylation described hereinbefore the relative bulkiness of the alkylating agent influences the ratio of the enol ethers formed, i.e. the ratio of the substituted C-1 enol ether relative to the substituted C-3 enol ether. For example, with isopropyl iodide as the alkylating agent and 2(6'-carbomethylhexyl)-4(R)-hydroxy-2-cyclopentane-1,3-dione as the substrate the two enol ethers

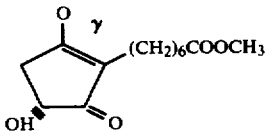

A and

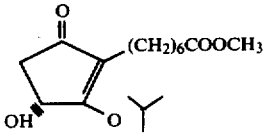

B were formed in the ratio of A:B of 6:4; however, when isoamyl iodide, a bulkier grouping, was used as the alkylating agent the ratio of the desired substituted C-1 enol ether to the substituted C-3 enol ether was about 7:3.

The following table will indicate the relative proportions of the enol ethers obtained with the indicated alkylating agents:

| Agent (R'I) | 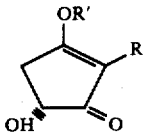 (Preferred ether) | 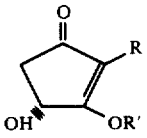 |
|---|---|---|
| 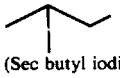 (Sec butyl iodide) | 40% | 60% |
| 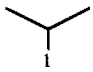 (isopropyl iodide) | 60% | 40% |
| 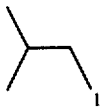 (isobutyl iodide) | 70% | 30% |
| 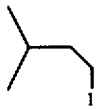 (iso amyl iodide) | 70% | 30% |

It will be obvious to those skilled in the art that instead of the O-acylation or O-alkylation described hereinbefore selective formation of enamines or silanes will suitably function for the purposes of this invention. For example, in place of the aforementioned acylating or alkylating agents pyrrolidine or morpholine or the conventional silating agents can be used in the enolization procedures.

Reduction of the substituted C-1 enol ester or enol ether can be readily accomplished with sodium dihydro-bis (2-methoxyethoxy) aluminate (termed the Red-Al agent) as shown by Pappo et al., Tetrahedron Letters, No. 26, p. 2627 (1972), Pergamon Press. Other reducing agents, such as, for example, lithium borohydride, diisobutyl aluminum hydride and lithium aluminum hydride, are also capable of reducing the carbonyl function of the substituted C-1 enol ester or ether in accordance with the procedures of this invention to produce the desired 2-substituted-4(R)-hydroxy-2-cyclopenten-1-one products.

The following Examples are presented by way of illustration only and are not in any way to be construed as limiting the scope of the invention defined in the appended claims.

EXAMPLE 2

Preparation of the Di-enol benzoates

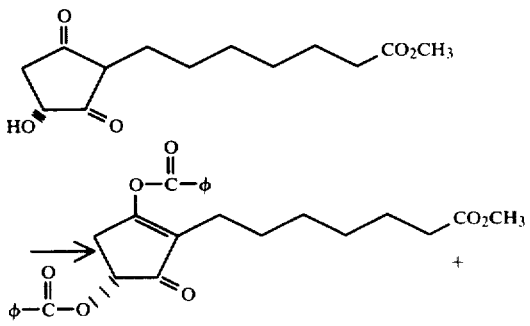

II

III a

-continued

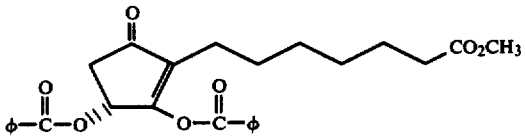

III b

To a solution of 120 mg (0.467 mmole) of 2(6'-carbomethoxyhexyl)-4(R)-hydroxy-cyclopentane-1,3-dione (II), 0.4 ml (~3 mmole) triethylamine ($Et_3N$) (distilled over $CaH_2$) in 10 ml tetrahydrofuran (THF), cooled to −15° was added 0.5 ml (4.34 mmole) benzoyl chloride over a 5 minute period with stirring. After the reaction mixture was stirred at −15° to 5° C. for 3 hours, water was added and the mixture was extracted 3 times with diethyl ether. The ethereal layer was washed successively with dilute HCl water, saturated $NaHCO_3$ and NaCl solutions. The ether layer was then dried over $Na_2SO_4$ and evaporated to dryness. Proton magnetic resonance (PMR) analysis showed the dried product contained 90% of the desired substituted C-1 dibenzoate (IIIa) which can be readily separated by column chromatography using a silicic acid-Celite (85:15) column (21×2.5 cm) with a benzene-ethyl acetate gradient as set forth in Example 4.

EXAMPLE 3

Preparation of the acetyl enol ether

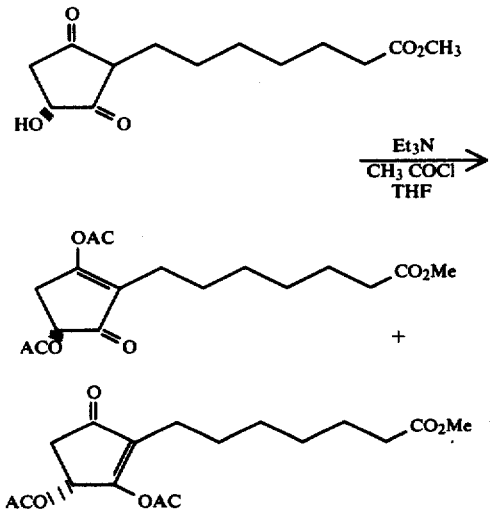

II

IIIc

IIId

To 118 mg of II (0.46 mmol), 0.4 ml (3 mmol) $Et_3N$ (freshly distilled over $CaH_2$) in 10 ml THF was added 0.3 ml of acetyl chloride over a 3 minute period (dropwise) with stirring at −5° C. The reaction was allowed to proceed for 4 hours (convenience) after which two ml of methanol was added and the reaction mixture was stirred at 0° C. for 15 minutes. Water was then added to the mixture. The mixture was extracted twice with diethyl ether, and the ethereal layer was washed successively with dilute HCl, water and $NaHCO_3$ (saturated solution). The ethereal fraction was dried over sodium sulfate and concentrated in vacuo to yield 140 mg of orange oil. PMR analysis indicated that the oil comprised 70–75% of the desired enol ether (IIIc). Separation of IIIc from IIId can be readily accomplished by chromatography in the system described in Example 2.

EXAMPLE 4

Preparation of the t-Butyl-enol ester

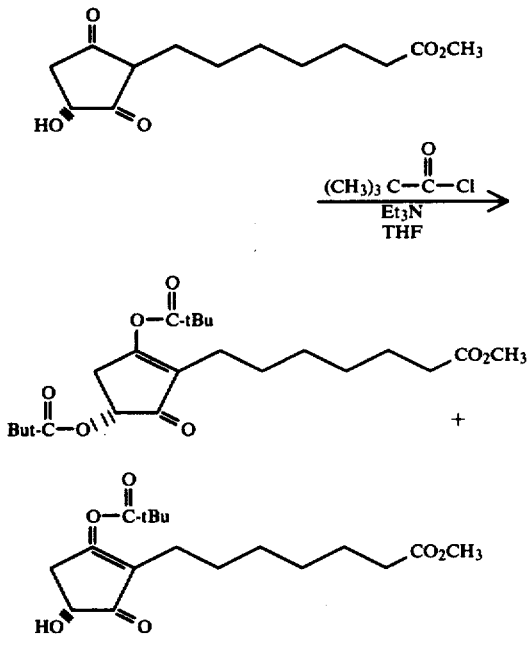

II

IIIe

IIIf

To a solution of 0.512 g (2 mmol) of II, and 1.74 ml (ca.13 mmol) $Et_3N$ (distilled from $CaH_2$) in 40 ml of THF, cooled to −15° C. was added 1.1 ml (9.06 mmol) of pivaloyl chloride over a 10 minute period with stirring. This solution was stirred at −15° to 0° C. for 3 hours. Following the same work-up procedure as in Example 2, the dried residue (500 mg) was dissolved in benzene and chromatographed in a silicic acid-Celite (85:15) column (21×2.5 Cm). The column was eluted with a gradient system consisting of 300 ml of benzene in the mixing chamber and 300 ml of 30% ethyl acetate on benzene in the reservoir flask. 7 ml fractions were collected. Fractions 25–36 (251 mg) consisted of the diacyl derivative (IIIe). PMR showed two t-Butyl groups at δ1.21 and 1.32, ester methoxy at δ3.66 and a proton at δ5.25 (dd, J=3.5, 7). Fractions 55–73 (264 mg) consisted of IIIf, the desired product. PMR showed only one t-Butyl group at δ1,30, ester $OCH_3$ at δ3.67, one proton at ca.δ83.4 (broad OH), and one proton at δ4.38 (dd, J=3.5, 7), consistent with IIIf. There was no trace of the isomeric enol ester derivative.

EXAMPLE 5

Preparation of the mono-enolbenzoate ester

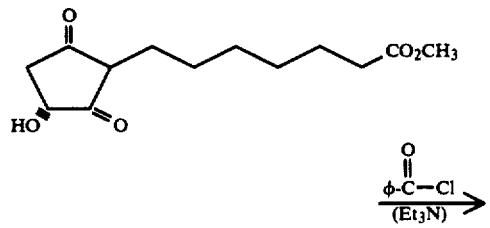

II

-continued

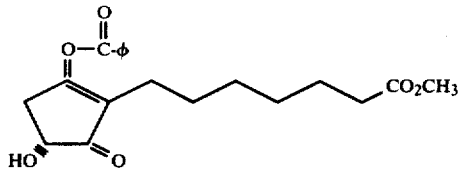

IIIg

To a cooled (−11° C.), stirred solution of 102.4 mg (0.4 mmoles) of the hydroxydione methyl ester (III) and 0.112 ml ca 0.84 mmoles) of triethylamine (distilled over calcium hydride) in 8 ml dry tetrahydrofuran (under $N_2$), was added 0.046 ml (0.4 mmoles) of benzoyl chloride over 5 minutes. The resulting solution was stirred at −10° C. for 35 minutes. 4 ml of methanol was added and the solution allowed to warm to room temperature, and then poured into 60 ml water. This solution was extracted 4 times with 50 ml of ethyl acetate each time and the combined extract washed successively with 0.1N HCl (10 ml), water (10 ml), saturated sodium bicarbonate (10 ml) [The sodium bicarbonate washing was acidified and extracted with ethyl acetate. The extract was washed with a saturated sodium chloride solution and dried ($MgSO_4$). Evaporation of the solvent gave unreacted hydroxy dione methyl ester (30 mg) II] and saturated sodium chloride (10 ml) solutions and dried over $MgSO_4$. Evaporation of the solvent gave a yellow oil having the following characteristics: PMR δ3.65 (S, 3H, $O\underline{CH_3}$); δ4.48 (q, 1H, H—C—OH); 87.70 (m, 3H) and δ8.18 (m, 2H) aromatic Protons, m/e at 360; $[\alpha]_D^{24}+35°$(C, 2.0 $CHCl_3$); $\gamma_{max}^{alc}$ 241 nm (ε20,100); (S) 270 nm (ε8,500) which identified the product as IIIg.

EXAMPLE 6

Preparation of the Isopropyl Enol-ether

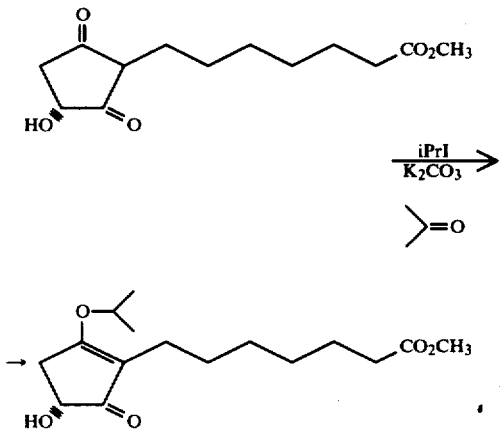

II

IIIh

To 514 mg of the hydroxydione ester (II) (2.0 mmole), was added 546 mg of $K_2CO_3$ (4 mmol), and 5 ml (8.5 g, 50 mmole) isopropyl iodide in 25 ml of dry acetone. The mixture was heated under reflux ($N_2$ atmosphere) for 24 hours. After cooling, the reaction mixture was diluted with $Et_2O$ and the ethereal layer was washed successively with water, $NaHCO_3$, water and saturated NaCl. The solvent layer was then dried over $Na_2SO_4$ and evaporated to dryness to yield 560 mg of an oily residue. The residue was dissolved in isopropyl ether to yield 316 mg (53%) of a product having the following characteristics; m.p. 60°-62° C.; $\gamma_{max}^{alc}$ 259 nm (ε20,600); PMR ($CHCl_3$)1.35

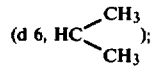

δ3.65 (S, 3, $COOCH_3$); δ4.32 (q, 1, >$C\underline{H}$OH); δ4.67

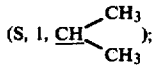

m/e 298; $[\alpha]_D^{24}+35.1$ (C, 1.02 MeOH); which identified it as IIIh.

EXAMPLE 7

Preparation of the Isoamyl enol ether

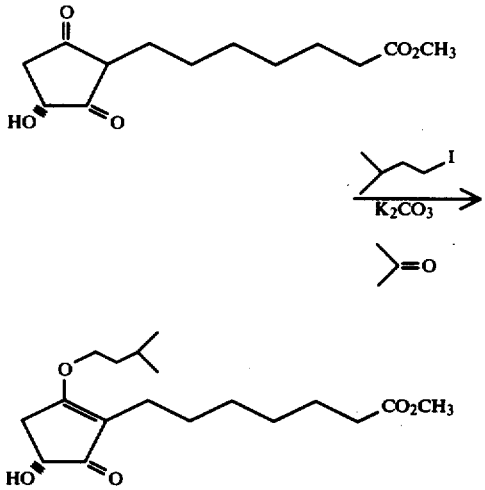

II

IIIi

To 121 mg of II, 287 mg of $K_2CO_3$ in 15 ml of dry acetone was added 2 ml of isoamyl iodide. After refluxing overnight, the reaction mixture was worked up as in Example 5. The residue weighed 165 mg. PMR analysis revealed an isopropyl doublet (δ0.95J=6HZ), complex region (γ1.1-3.1), methoxyl (δ3.65), multiplet (~δ4.0−4.5, ca 3H based on methoxyl), and a broad doublet (γ5.0, J=6) (30% of 1H, based on methoxyl), ca 4H total integral from δ4.0 to δ5.10 - indicating the inclusion of —OH, —$OCH_2$—$CH_2CHMe_2$ and OH—$\underline{CH}$<. THus, the product was determined to contain about 70% of the desired substituted C-1 enol ether IIIi, which is readily separated from the substituted C-3 enol ether by column chromatography as described in Example 4.

EXAMPLE 8

Reduction of the mono-enolbenzoate ester with "Red-Al"

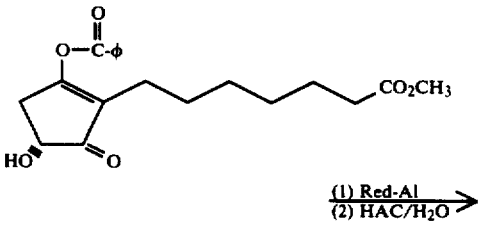

IIIg

-continued

IV

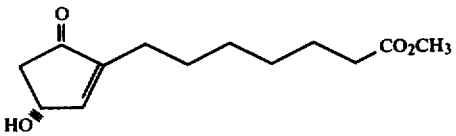

To a cooled (−78° C.), stirred solution of 50 mg (0.147 mmoles) of mono-enolbenzoate (IIIg) in 10 ml of dry tetrahydrofuran under $N_2$, "Red-Al" solution (1.5 M in toluene) was added in four 0.38 ml aliquots over 15 minutes. The resulting solution was stirred at −78° C. for a further 30 minutes. Two ml of glacial acetic acid was added and the solution was allowed to warm to room temperature. The solution was poured into 40 ml of water and extracted with ethyl acetate (4×30 ml). The ethyl acetate layer was washed with 10 ml each of saturated sodium bicarbonate and saturated NaCl solutions and dried over $MgSO_4$. Evaporation gave an oil. The oil was dissolved in 10 ml acetic acid-water (75:25) solution. The resulting solution was stirred at room temperature for 24 hours. The acetic acid-water were evaporated off under reduced pressure. The resulting oil was dissolved in ethyl acetate (10 ml) and washed with saturated sodium bicarbonate and saturated sodium chloride solutions and dried over $MgSO_4$. Evaporation of the solvent gave a yellow oil (ca25–30 mg). Crystallization from ethyl acetate-Skelly B afforded 20 mg of IV, which was identified by the following characteristics: m.p. 60°–61° C.; $[\alpha]_D^{24}=+17.82°$(C, 0.49 MeOH); PMR ($CDCl_3$) δ3.65 (S, 3 $COOCH_3$), δ4.93 (m, 1, H—C—OH), δ7.23 (m, 1 Vinyl H); uv $\gamma_{max}^{MeoH}$ 222 nm (ε8,400) CD 231 nm $6-9.9°\times10^{-3}$ (MeoH).

EXAMPLE 9

Reduction of the Isopropyl-enol ether with Red-Al

IIIh

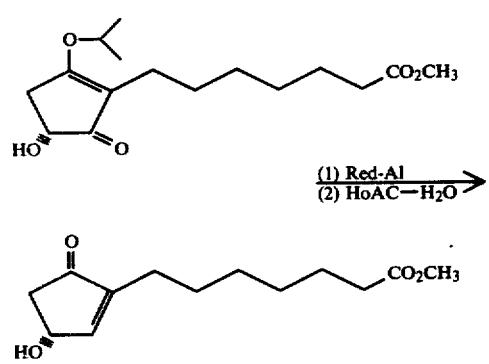

IV

To 123 mg of the isopropyl enol ether (IIIh) (0.412 mmol) in 10 ml of THF, stirred under $N_2$ at −78° C., four 1.1 ml aliquots of a solution of Red-al in benzene (1.5M) was added dropwise over a 7 minute period. The reaction mixture was stirred at −78° C. for 45 minutes and 2 ml of acetic acid was then added. The reaction mixture was allowed to warm to room temperature and evaporated to dryness. Ten ml of 75% acetic acid solution was added and stirred for 24 hours. The acetic-and-water were evaporated off under pressure. The resulting oil was dissolved in ethyl acetate (25 ml) and washed with saturated $NaHCO_3$ and NaCl solutions and then dried over $MgSO_4$. Crystallization of the residue from ethyl acetate - Skelly B afforded IV (60 mg), which was identified by the following characteristics: m.p. 60°–61° C.; $[\alpha]_D^{24}+17.82°$(C, 0.49 MeoH); $\gamma_{max}^{alc}$ 222 mn (δ8,400); CD 231 nm $\theta=-9.9°\times10^{-3}$ (MeoH).

The conversion of the compounds produced in accordance with the processes of this invention, namely, 2-substituted-4(R)-hydroxy-2-cyclopenten-1-one, to prostaglandins or prostaglandin-like compounds can be carried out in accordance with the process of Charles J. Sih et al., J. Amer. Chem. Soc., 94, 3643, May 17, 1972. Thus, once the above stereospecific compound is obtained the conversion to prostaglandins or prostaglandin-like compound can be readily accomplished with retention of the desired stereospecificity.

In addition to having utility as an intermediate in the syntheis of prostaglandins 1-isopropoxy-2-(6'-carbomethoxyhexyl)-4(R)-hydroxy-1-cyclopenten-3-one (the isopropyl enol ether) was found to have antimicrobial activity as shown in the following example.

EXAMPLE 10

23 mg of 1-isopropoxy-2-(6'-carbomethoxyhexyl)-4(R)-hydroxy-1-cyclopenten-3-one was dissolved in one ml of methyl alcohol. 0.1 ml of the resulting solution was applied to a filter paper disk (12.7 mm) and the disk was then dried. Each of the dried disks was then placed in a petri dish containing 10 ml of antibiotic medium II (Difco) to which had been added 0.03 ml of an inoculum of the test organism. The petri plates were incubated as 25° C. for 48 hours and the zone inhibition was measured with the following results:

| Test Organism | Zone Diameter |
|---|---|
| E coli | No zone |
| B cereas | 19.5 mm |
| B subtilis spores | 16.5 mm |
| Staphylococcus aureus | 21.0 mm |
| Sarcina lutia | 15.0 mm |

Having thus described the invention, what is claimed is:

1. A method for preparing 2-substituted-4(R)-hydroxy-2-cyclopenten-1-one which comprises:

preparing 2-substituted-4(R)-hydroxy-cyclopentane-1,3-dione by a method selected from the group consisting of a. catalytically hydrogenating a compound of the formula

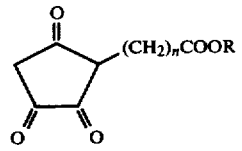

where

R is selected from the group consisting of a hydrocarbon radical containing from about 1 to 4 carbon atoms and benzyl and n is an integer from about 1 to 12, the hydrocarbon chain represented by $(CH_2)_n$ being saturated or containing a cis double bond or triple bond at the 5–6 position in the equivalent acid side chain represented by $(CH_2)_nCOOH$ in the presence of a rhodium complex with a catalyst comprising a chiral phosphine ligand;

b. subjecting 2-substituted cyclopentane-1,3,4-trione or 2-substituted-3-alkoxy-2-cyclopentane- 1,4-dione to the fermentative enzymatic action of a microorganism of the class Ascomycetes; and c. resolving 2-(6'-carbomethoxyhexyl)-4-hydroxycyclopentane-1,3-dione with brucine and recovering the corresponding 2-substituted-4-(R)-hydroxy-cyclopentane-1,3-dione enolizing the said dione by reacting it under basic conditions with compounds selected from the group consisting of

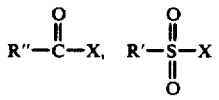

where X is selected from the group consisting of I, Cl, Br,

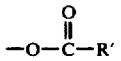

and $—OSO_2R'$ and

R' is selected from the group consisting of pivaloyl, isobutyl, phenyl, benzyl, bipenyl, naphthyl, alkanyl and alkenyl having from about 1 to 6 carbon atoms, and halogen-, *alkyl- and alkoxy-substituted phenyl, benzyl,* biphenyl and naphthyl groups, and R''X where R'' is selected from the group consisting of saturated and unsaturated alkyl having from about 1 to 6 carbon atoms, benzyl, diphenylmethyl, $CH_2COOR'''$ and R'''—CH—COOR''' where R''' is a hydrocarbon radical containing from about 1 to 6 carbon atoms, and X is selected from the group consisting of Cl, Br, I, sulfate, isocyanate, aryl sulfonate and alkyl-substituted aryl sulfonate radicals to preferentially promote acylation or alkylation of the oxygen atom at the C-1 position of the dione recovering the substituted C-1 enol reducing the said substituted C-1 enol with a hydride reducing agent and recovering 2-substituted-4(R)-hydroxy-2-cyclopenten-1-one from the reduction reaction mixture.

2. The method of claim 1 wherein the 2-substituent on the trione and the 2-substituted-3-alkoxy-2-cyclopentane-1,4-dione is the 6'-carbomethoxyhexyl group and 2-(6'-carbomethoxyhexyl)-4(R)-hydroxy-2-cyclopenten-1-one is recovered as the desired product.

3. The method of claim 2 wherein enolization to the enol ester configuration is accomplished by reacting the dione with pivaloyl chloride.

4. The method of claim 2 wherein enolization to the enol ether configuration is accomplished by reacting the dione with isoamyl iodide.

5. The method of claim 2 wherein enolization to the enol ether configuration is accomplished by reacting the dione with isopropyl iodide.

6. The method of claim 2 wherein enolization to the mono-enolbenzoate ester configuratin is accomplished by reacting the dione with one molar equivalent of benzoyl chloride.

7. The method of claim 2 wherein the enolization to the di-enol-benzoate ester configuration is accomplished by reacting the dione with two molar equivalents of benzoyl chloride.

8. The method of claim 2 wherein enolization to the enol ester configuration is accomplished by reacting the dione with acetyl chloride.

9. The method of claim 2 wherein the reduction of the enol ester or enol ether is accomplished by reacting the said ester or ether with sodium dihydro-bis(2-methoxyethoxy)aluminate.

* * * * *